Figure 1:
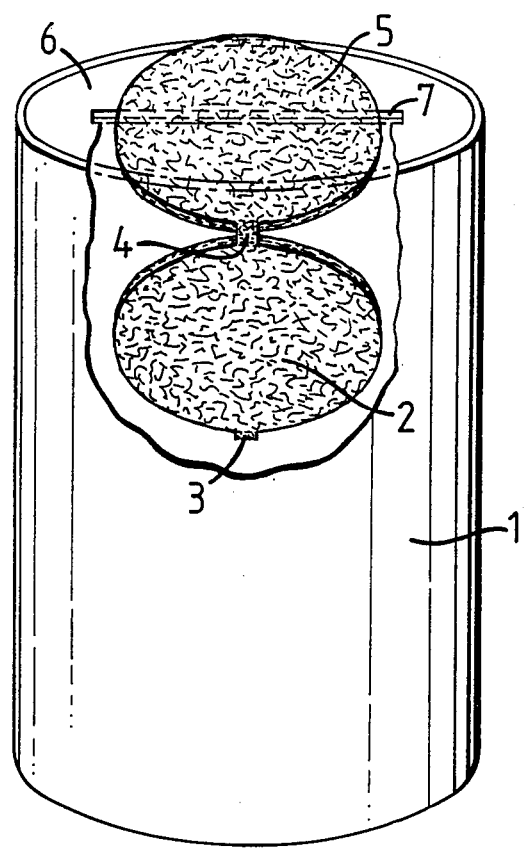

United States Patent [19]

Burgin

[11] Patent Number: 4,927,064

[45] Date of Patent: May 22, 1990

[54] CURVED DISPENSIBLE PADS

[75] Inventor: Robert Burgin, Schaffhausen, Switzerland

[73] Assignee: IVF Maschinenfabrik Schaffhausen, Switzerland

[21] Appl. No.: 221,712

[22] Filed: Jul. 20, 1988

[30] Foreign Application Priority Data

Jul. 21, 1987 [GB] United Kingdom ................. 8717143

[51] Int. Cl.⁵ .............................................. B65D 5/72
[52] U.S. Cl. ..................................... 225/106; 221/63; 206/820
[58] Field of Search ...................... 225/1, 106; 221/47, 221/48, 51, 63; 206/820, 210, 494

[56] References Cited

U.S. PATENT DOCUMENTS

| 1,873,399 | 9/1932 | Hope | 225/106 |
| 2,823,089 | 2/1958 | De Franco | 225/106 |
| 3,161,336 | 12/1964 | Loescher | 225/106 |
| 3,749,296 | 7/1973 | Harrison | 225/106 |
| 3,780,908 | 12/1973 | Fitzpatrick et al. | 225/106 |
| 4,159,772 | 7/1979 | Beck | 221/63 |
| 4,219,129 | 8/1980 | Sedgwick | 221/63 |

Primary Examiner—Frank T. Yost
Assistant Examiner—Scott A. Smith
Attorney, Agent, or Firm—Ostrolenk, Faber, Gerb & Soffen

[57] ABSTRACT

A stack of cosmetic pads (2) of an arcuate configuration conjoined by one bridgeable members (3) for "one-handed" individual dispense via dispense slot (7).

2 Claims, 3 Drawing Sheets

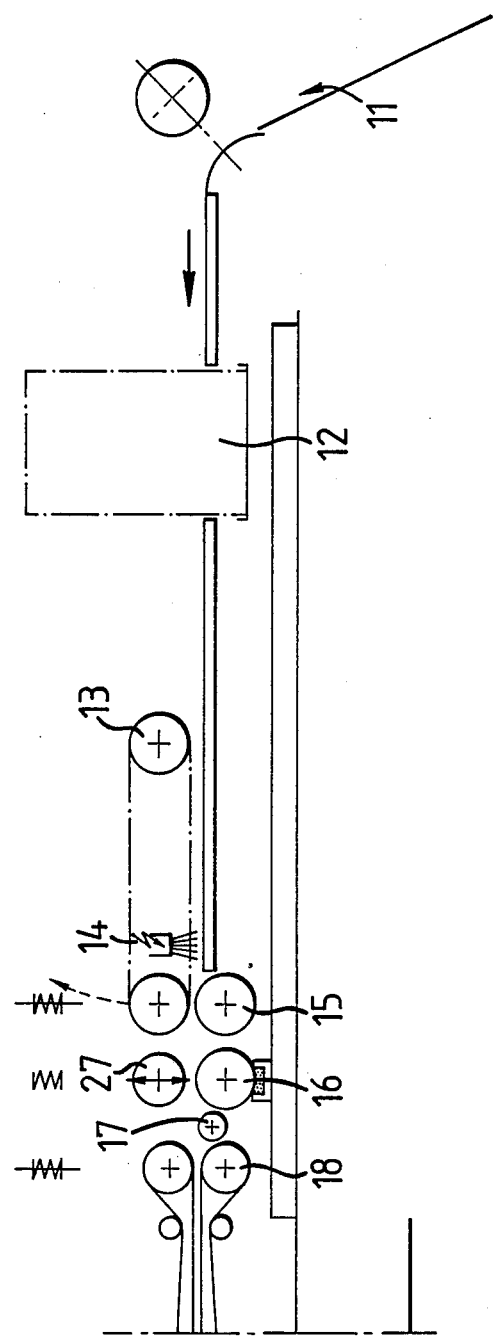

CURVED DISPENSIBLE PADS

DESCRIPTION

The present invention relates to curved dispensible pads, and particularly to curved absorbent pads for medical use.

The invention also relates to stacks to such pads in a suitable dispensing container which can be readily dispensed.

In the field of dispensing pads, particularly absorbent pads, it is well known to provide a stack of pads interleaved with each other so that the removal of an uppermost pad leaves the free edge of the underlying pad readily accessible. The preparation of such stacks, however, requires the utilization of complicated folding machines and is anyway not appropriate for pads which are other than rectilinear.

It is also known to provide a folded stack of pads, each conjoined to the other via a line of perforations. It will be appreciated that the line of perforations may be considered as a line of frangible bridges conjoining each sheet to an adjacent sheet. When pulled in a direction perpendicular to the line of perforations the frangible bridges are in practice substantially as strong as the web in which they are formed. Accordingly, "a straight pull" perpendicular to the perforations will only separate a first sheet from a second sheet with difficulty. However, where the frangible bridges are subjected to an angled force as achieved by pulling the pad in a direction other than perpendicular to the line of perforations all the force will fall on the first frangible bridge causing this to fracture and to load the next succeeding bridge and accordingly the pad is readily separated.

This arrangement allows the pads to be separated on a "one-handed" basis.

The substantially rectilinear pads, according to the prior art, have the disadvantage, however, that there is a substantial waste of material in practice. This is because when these pads are used for absorbent purposes as in mopping up biological material the only portion to be actually used is the central portion of the pad. It has been found that circular, or at least pads with arcuate edges are more readily inserted into less accessible positions during, for example, infant care.

Circular or ellipsoidal pads are in fact available as a stack of unconnected absorbent pads. Because the pads are not connected to each other there are difficulties in dispensing the same, particularly on a "one-handed" basis.

Accordingly, there is a need to provide a stack of absorbent pads connected to each other which can be dispensed on a "one-handed" basis. The line of perforations is not appropriate because of the shape of the absorbent pads, the frangible bridges must be strong enough to withstand a pull along the longitudinal axis of the conjoined stack of absorbent pads but without the advantage of being able to separate adjacent pads by a pull angled to the said axis as would be appropriate in pads of a rectilinear shape.

According to the present invention, therefore, there is provided a plurality of stackable absorbent pads having opposed arcuate edges, characterised in that each pad is conjoined to the immediately adjacent pads by frangible bridge portions disposed on its arcuate edges and characterised in that the material which makes up the pads and the frangible bridge portions is homogenous throughout the stack.

Preferably each frangible bridge is positioned along a common axis for all frangible bridges, preferably it has a breaking strain of between 200 and 400 gms.

Preferably the stack of pads is contained within a tubular container having a dispensable port at one end thereof. The pads may then be sequentially presented at the port for dispensing.

Preferably the action of withdrawing a first pad from the port has the effect of partially withdrawing the next pad for dispense before causing the frangible bridge to fracture to release the withdrawn pad from the stack. Accordingly the frangible bridge must have a strength sufficient to dislodge the next pad through the dispense port, but insufficient to withdraw the pad completely before breakage when pulled generally transversely.

The pads in accordance with the present invention are preferably circular or ellipsoidal, but of course can be any shape which terminates at one end in an arcuate surface. The pads are preferably formed at least partly of a fibrous material wherein at least 10% of the material has a minimum length of 5 mm. The pads are preferably die cut from a sheet material of this last type in such a way that the pads are linked in preselected locations by fibres running from one pad to the next (i.e. the pads share common elongate fibres). The orientation of the fibres in the material may be parallel, random or diagonal, given that a given portion are elongate over the bridge portions.

The fibres may adhere together either by entanglement, by fusible material in the fibres, or by binders or by a mixture of any of them.

According to a second feature of the present invention, there is provided a dispensing pack for a stack of pads having opposed arcuate edges conjoined by a frangible bridge portion immediately adjacent the pads which overlie each other on a common axis, said pack comprising a container for said stack terminating at one end in an elongate dispense slot; characterised in that the stack and the slot co-operate in use such that withdrawal of the uppermost pad in a direction orthogonal to the axis of the stack and the slot causes the penultimate pad to be folded over the edge of the slot so that the frangible bridge fractures before the penultimate pad is withdrawn. Preferably the frangible bridge will withstand a straight pull of between 200 and 400 gms. but figures of, for example 100 to 500 gms are sometimes appropriate. In some particular circumstances this figure may be between 50 gms and 1 kilo.

According to a third aspect of this invention, there is provided a method for the dispense of linked absorbent pads from a stack thereof contained within a container having an elongate dispense aperture which method comprises gripping a first pad protruding from the dispense aperture and withdrawing the same substantially along the axis of the stack until a significant portion of the next succeeding pad has been withdrawn through the aperture, and then subsequently changing the direction of pull from axial to generally transverse thereby to fracture the frangible bridge linking the pad to be dispensed from the next succeeding pad.

According to a fourth aspect of the invention there is provided an apparatus for the production of a stack of pads of an arcuate transverse cross section, which apparatus comprises; means for the supply of a sheet web to a continuous cutting roller to form the web into an elongate succession of pads conjoined by bridge portions; belt means for feeding said cut web to pleating rollers, packing means adapted to coact with the pleating rollers to cause said pads to concertina along a common axis, and bagging means to receive and retain the concertinered sack under compression.

Although this invention has been described with reference to an elongate dispensing slot it will, of course, work with slots of a different configuration so long as the pads can be readily withdrawn in an axial direction and separated by a transverse or an orthogonal pull.

It will also be appreciated that a preferred embodiment of the invention is a pad not only absorbent but also resilient. Accordingly, the upper pads at least tend to be held against the underside of the end face adjacent the dispense aperture which ensures that the penultimate pad is bent to a right angle during the generally transverse or orthogonal pull to separate it from the pad to be dispensed. The fibres useful in this invention include cellulose or synethic fibres or blends thereof (e.g. cotton or regenerated cellulose).

Figure 2A:
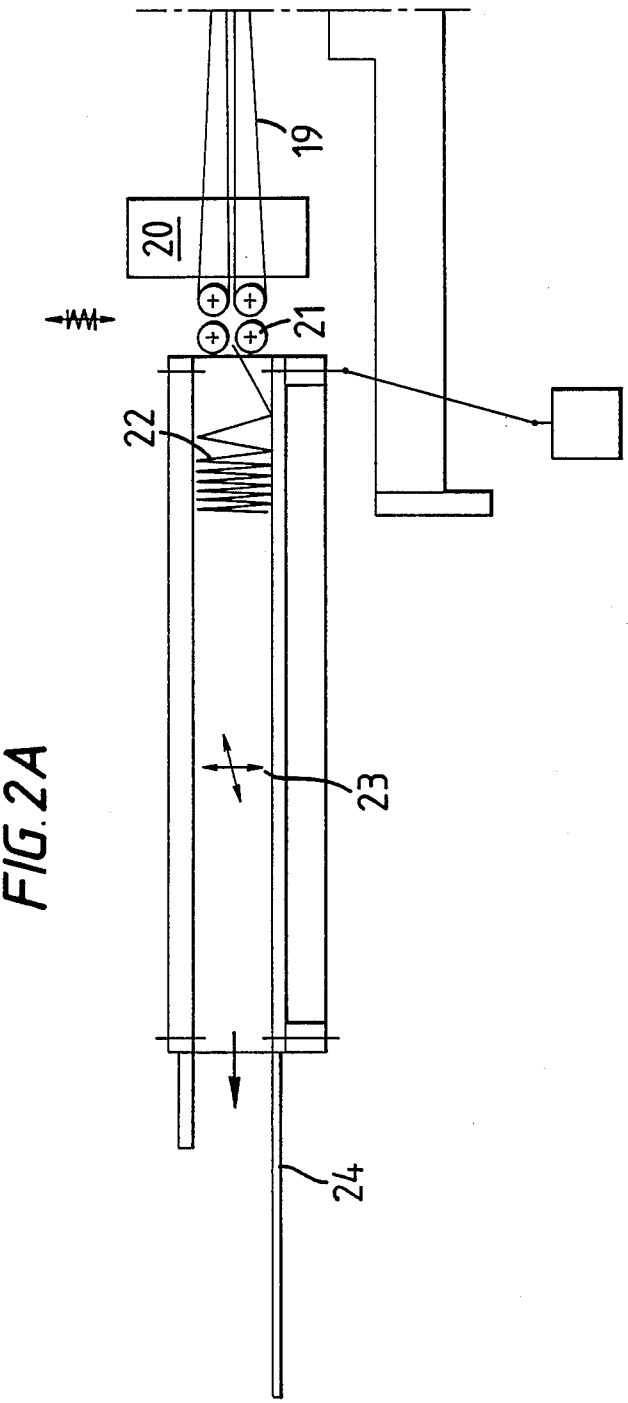

The invention will now be described, by way of illustration only, with reference to the accompanying drawings wherein FIG. 1 shows a side elevational view of pads in accordance with the present invention being withdrawn from a contained stack thereof, and FIGS. 2a and 2b show a diagrammatic side elevation of a stack forming apparatus in accordance with a further feature of this invention.

With reference to FIG. 1 of the accompanying drawings a plurality of absorbent pads for medicinal purposes (2) of a generally ellipsoidal configuration are stacked one upon the other conjoined by frangible bridges (4). Each of said pads (2) overlies the succeeding and preceding pads in precise register. The pads (2) in accordance with the present invention are contained within a container (1) which may be of any convenient construction, is preferably tubular so as to hold the pads (2) in register one upon the other. The container (1) is provided at one end with elongate dispense slot (7) disposed across an end face (6).

In use the first pad (2) is presented with a portion thereof protruding from the slot (7), undispensed pad (2) is grasped, pulled upwardly along the axis of the stack. As the pad (2) is withdrawn it leads the next succeeding pad (5) through the slot (7), such that approximately half of the pad protrudes therefrom. The direction of pull is then changed from axial to orthogonal so as to bend the pad (5) about the edge of the slot (7). If the pulling force is then increased somewhat the frangible bridge (4) will fracture, thereby releasing the pad (2) and leaving the pad (5) with a portion thereof extant for ready gripping so that the process may be repeated. The bridge (4) has a breaking strength of approximately 300 gms. which is sufficient to allow the pads tobe withdrawn from the stack in the axial direction without fracturing, but sufficiently low to allow the pads to be readily broken at the frangible bridge (4) when a force in excess of 300 gms. is applied.

This process allows the pads to be dispensed on a "one-handed" basis since with the container (1) fixed it is only necessary to apply the axial force upwardly followed by an orthogonal force to release a pad for use.

With reference to FIGS. 2a and 2b a stack forming apparatus in accordance with the present invention provides a material feed (11) to supply a fibrous web of for example cotton via an electronic cotton wool balance (12) to feed rollers (13) which act to supply an elongate web of the absorbent cotton material. A sensor (4) is provided downstream of the feed rollers (13) in order to ensure that the cotton web is present. Brakes in the web sensed by the sensors (14) can be dealt with, usually by switching off the drive rollers (13).

The web on passing the sensors (14) passes between embossing rollers (15) and between cutting rollers (16) which cut the web into a continuous strip of elongate bridges adjoining cotton pads of arcuate configuration. Knives (27) can be utilized to sever the web in its entirety at a predetermined distance in accordance with the intended size of the stack. The so formed cut web is conveyed by rollers (17) transport rollers (18) via pleating belts (19) to a pleating apparatus (20). Pleating apparatus (20) comprises pleating rollers (21) which are so arranged as to concertina the pads as shown at (22) into a stack. A bag is disposed over the support (24) whereby the concertinered pads (2) are fed under compression into the bag and are held under compression in said bag in each of their lengths determined by the knives (27).

An apparatus in accordance with this invention allows the curved pads in accordance with the present invention to be formed into a concertinered stack under compression on a simple basis. The curved pads in accordance with the invention can of course be replaced, by suitable engineering changes by a pad of any configuration.

The invention provides, therefore, a stack of conjoined absorbent pads overlaying each other in register, a container containing the same, with a dispense opening, and method for releasing pads from a stack using such a connotation of parts.

I claim:

1. A dispensing system, comprising:
    a stack of pads overlying one another and stacked on a common axis, each of the pads having arcuate edges and the opposed arcuate edges of adjacent pads in sequence in the stack being joined by a single frangible bridge immediately between and adjacent the pads; and
    a container for the stack, the container terminating at one end and toward one end of the stack in an elongate dispensing slot so that the pads are withdrawn in sequence through the slot;
    the stack and the slot cooperating in use so that withdrawal of the then uppermost pad in a direction generally transverse to the axis of the stack and the slot causes the then next pad in the stack to be folded over the edge of the slot for fracturing the frangible bridge before that next pad is withdrawn;
    the pads being formed from a resilient absorbent fibrous material in which elongate fibers run from one pad to the next pad via the frangible bridge and the frangible bridge is shaped and sized so that with the quantity and nature of the fibers running through the bridge, the bridge will withstand a straight pull between 200 and 400 grams, the material which makes up the pads and the frangible bridge being homogenous throughout the stack of pads.

2. A system according to claim 1 wherein the resilient fibrous absorbent material is formed from fibers which are random, parallel and diagonally oriented with respect to the edges of said pad wherein some of the fibers are elongate over the bridge.

* * * * *